US 6,616,604 B1

(12) United States Patent
Bass et al.

(10) Patent No.: US 6,616,604 B1
(45) Date of Patent: Sep. 9, 2003

(54) SURGICAL RETRACTOR SECURING APPARATUS

(75) Inventors: Daniel Bass, El Granada, CA (US); Udo Wiedenmaier, San Mateo, CA (US)

(73) Assignee: Allegiance Corporation, McGaw Park, IL (US)

( * ) Notice: Subject to any disclaimer, the term of this patent is extended or adjusted under 35 U.S.C. 154(b) by 0 days.

(21) Appl. No.: 10/117,285

(22) Filed: Apr. 5, 2002

(51) Int. Cl.⁷ .................................................. A61B 1/32
(52) U.S. Cl. .................................... 600/206; 600/233
(58) Field of Search ........................... 600/206, 215, 600/217, 227, 231, 232, 233, 236

(56) References Cited

U.S. PATENT DOCUMENTS

| | | | | |
|---|---|---|---|---|
| 4,051,844 A | | 10/1977 | Chiulli ........................ 128/20 |
| 4,430,991 A | * | 2/1984 | Darnell | |
| RE32,021 E | * | 11/1985 | Scott, Jr. | |
| 4,621,619 A | | 11/1986 | Sharpe ........................ 128/20 |
| 4,834,089 A | | 5/1989 | Koivukangas et al. ...... 128/303 |
| 5,052,374 A | | 10/1991 | Alvarez-Jacinto ............ 128/20 |
| 5,529,358 A | | 6/1996 | Dinkler et al. .............. 600/233 |
| 5,899,853 A | * | 5/1999 | Fowler, Jr. ................. 600/217 |
| 6,168,596 B1 | | 1/2001 | Wellisz et al. ................. 606/69 |
| 6,246,900 B1 | | 6/2001 | Cosman et al. ............. 600/426 |
| 6,309,387 B1 | | 10/2001 | Eggers et al. ................. 606/41 |
| 6,328,743 B2 | | 12/2001 | Lerch .......................... 606/72 |
| 6,333,971 B2 | | 12/2001 | McCrory et al. ........... 378/162 |
| 6,351,662 B1 | | 2/2002 | Franck et al. ............... 600/429 |
| 6,355,049 B1 | | 3/2002 | Gill ............................ 606/130 |

OTHER PUBLICATIONS

Dr. Sugita, Multi-Purpose Head Frame for Microneurosurgery.

* cited by examiner

*Primary Examiner*—Cary O'Connor
(74) *Attorney, Agent, or Firm*—Donald O. Nickey; Gallagher & Dawsey Co. LPA

(57) ABSTRACT

A surgical retractor securing apparatus includes an adjustable securing device which attaches the apparatus to the surgical accessory bar of a halo style head fixation device and a capture assembly that releasably engages the elasticized band of a scalp hook retractor. The adjustable securing device compressively grips along a portion the length of a surgical accessory bar or otherwise attaches to an external support, providing a plurality of attachment points. The capture assembly may include a pivotable cam that releasably grips the elasticized band of a scalp hook retractor by compressing the band between the gripping cam and the surgical accessory bar or other external support.

20 Claims, 4 Drawing Sheets

SURGICAL RETRACTOR SECURING APPARATUS

TECHNICAL FIELD

The invention relates to the field of surgical instruments, particularly, a device for anchoring surgical retractors during operative procedures.

BACKGROUND OF THE INVENTION

Medical professionals have long-recognized the need for surgical instruments that can be reliably placed and retained in position during surgery. What has been needed but was heretofore unavailable are surgical retractor anchoring devices that reliably retain retractors and are easily engaged and disengaged during surgery. Such long-felt needs have been particularly prevalent in the field of intracranial neurosurgery.

Surgical retractors designed to retract tissues during surgery may be generally classified into two types; those which are designed to be held free and manipulated by an assistant during surgery, and those that are attached to the patient, the operating table or other external support. This later class is styled in the art as self-retaining retractors. A common style of self-retaining retractor is exemplified by that disclosed by the Alvarez-Jacinto U.S. Pat. No. 5,052,374, where an annular ring supports substantially opposing retractors around an abdominal incision. The substantially opposing retractors are locked into place on the annular ring, commonly by ratchet devices as in Alvarez-Jacinto '374, or with a slide and thumbscrew assembly as taught by Sherts, et al., U.S. patent application Ser. No. US 2001/0009971 A1. These retractors are commonly designed to produce considerable and continuous pressure to retract strong tissues, such as the abdominal tissues described by Alvarez-Jacinto '374. Alternatively, a retractor may be fixed to the skin of the patient, such as that disclosed by Sharpe, U.S. Pat. No. 4,621,619. Alternatively, a retractor may be attached to the surgical drapes which cover the patient and operative field during surgery, such as that disclosed by Chiuli, U.S. Pat. No. 4,051,844.

Intracranial neurosurgery makes particular demands for the retraction of human tissue to allow the surgeon maximum access and stability of the surgical field. Due to the extremely delicate nature of the surgery, the surgical field, that is, the patient's head, must be held entirely immobile throughout the often lengthy procedure. Secondly, various tissues of differing tensile strengths, ranging from relatively strong scalp tissue to exceedingly delicate brain structures, must be retracted to allow surgical access during the procedure. The immobilization of the patient's head is commonly achieved by a halo style fixation device, such as that described by Dinkler et al., U.S. Pat. No. 5,529,358. Fixation devices, such as the screws disclosed in Dinkler et al., '358, attached the halo device to the bone of the patient's cranium, achieving positive fixation. The halo portion of the device surrounds the cranium, and may be adapted to hold various appliances during surgery, such as retractors, as further disclosed by Dinkler '358.

A particular demand of intracranial neurosurgery is the need to retract a flap of the patient's scalp away from the opening to be made through the bone of the patient's cranium. An incision is made about the sides and posterior border through the scalp, comprising the planned flap, and the flap is reflected away from the underlying bone anteriorly, maintaining a hinge-like attachment to the scalp, such that blood supply is preserved to the flap. The scalp flap, remaining attached at its anterior border, therefore has the tendency to fall back across the planned bone incision site, unless it is dependably retracted. The traditional means for accomplishing this intraoperative retraction is through the use of scalp hook retractors, which are devices well known in the art. These scalp hook retractors comprise a proximal sharp hooked portion made of a rigid material, such as surgical steel, attached to a distal elasticized band. The traditional application of these scalp hook retractors has been to evert the scalp flap away from the planned bone incision site, placing the proximal sharp hooked portion of the scalp hook into the underside edge of the scalp flap, and stretching the elasticized band of the scalp hook retractor away from the planned bone incision site. This action imparts a tensile stretch and pulls the edge of the scalp flap away from the planned bone incision site. The stretch of the elasticized band is maintained by looping or tying the elasticized band of the scalp hook retractor to the halo portion of the cranial fixation device. This allows the elasticized band of the scalp hook retractor to exert a continuous, but gentle, force on the edge of the scalp flap, retaining it away from the surgical site.

While effectively maintaining the scalp flap away from the surgical site, this means of attaching the elasticized band of the scalp hook retractor to the halo device creates several recurring problems. First, the attachment of the elasticized band of the scalp hook retractor to the halo device by tying or looping creates a potentially insecure attachment to the halo device, such that the elasticized portion of the scalp hook retractor may slip during surgery. Due to the extremely delicate nature of the surgery, such sudden motion in the surgical field can have disastrous consequences for the patient. Second, the nature of a halo style fixation device is that it provides a plurality of potential positions about the patient's skull such that the point of fixation of the scalp hook retractor, and thereby its vector of force, may be radially varied. However, to achieve such radial adjustment, repositioning the scalp hook retractor requires untying or unlooping the elasticized band and then re-tying or re-looping the elasticized band, a cumbersome and time consuming procedure, particularly if a plurality of scalp hooks need to be readjusted. Third, fixation by tying or looping makes it difficult for the surgeon to effectively select the amount of tension desired, as the length, and therefore tension, of the elasticized material will often change while manually tying or looping the elasticized material.

Accordingly, the art has needed a means for locking scalp hooks retractors in position, satisfying the need for a secure attachment, yet one that is easily releasable and adjustable by the surgeon.

What continues to be needed, but is missing from the field of surgical retractor anchoring devices, is a surgical retractor securing apparatus, which is designed for ease of use, manufacture, sterilization, and improved reliability that improves the capability for secure connections. While some of the prior art devices attempted to improve the state of the art of surgical retractor retaining devices, none has achieved a cost optimized capability that has an easy to fabricate and convenient to use arrangement. With these capabilities taken into consideration, the instant invention addresses many of the shortcomings of the prior art and offers significant benefits heretofore unavailable.

SUMMARY OF INVENTION

In its most general sense, the present invention overcomes the shortcomings and limitations of the prior art in any of a number of generally effective configurations. An aspect of this invention is to provide a scalp hook locking device that is capable of quickly and dependably locking the elasticized band of a scalp hook to an external fixation device.

A further aspect of this invention is to provide a surgical retractor securing apparatus such that the degree of tensile stretch upon the elasticized band of the scalp hook retractor may be easily selected and adjusted by the surgeon, and once selected, will be positively maintained. A yet further aspect of this invention is to provide an easily adjustable scalp hook locking device that may be varied in radial orientation around a patient's skull. Additionally, the present invention is designed to have flexibility of assembly, ease of cleaning and sterilization, ease of manufacturing, and low cost.

The surgical retractor securing apparatus includes an adjustable securing device and a capture assembly. The adjustable securing device is designed to grip and rigidly hold a surgical accessory bar or other external support. The capture assembly is designed to releasably retain the elasticized retractor band. As used herein and in the claims the term "elasticized band" includes rubber bands, elastic fabric, rope, string, suture thread, bungee cord, tape, cable, cloth, wire, springs, chains, and the like.

Thus, there is disclosed a surgical retraction securing apparatus adapted to be releasably secured to a surgical accessory bar and operative to releasably retain an elasticized band, comprising: 1) an adjustable securing device for gripping the surgical accessory bar at a proximal end of the adjustable securing device; and 2) a capture assembly mounted at a distal end of the adjustable securing device for releasably retaining the elasticized band.

In the preferred embodiment, the adjustable securing device may be configured to define an adjustable accessory bar receiver that substantially surrounds a surgical accessory bar that is part of a halo style head fixation device, well known in the art, used in intracranial neurosurgery. The adjustable securing device comprises a securing device compression area that can be manually compressed by an accessory bar compression adjuster that is threaded into the adjustable securing device to provide a compressive grip on the surgical accessory bar. The accessory bar compression adjuster, in the preferred embodiment, is provided with a thumbscrew and a tool engager at its distal end such that a tool may be used to increase the leverage in tightening and loosening the compression adjuster. In other embodiments, the securing device compression adjuster may include a thumbscrew configured with a high friction surface, wings, alternative shaped top with gripping edges, or other grip enhancing features.

The adjustable securing device is configured to have a partially open position at rest, such that a manual release of the accessory bar compression adjuster will result in a release of the compressive grip upon the surgical accessory bar. In alternative embodiments, the adjustable securing device may be configured to attach to external supports by an alternative mechanical no gripping assembly, including, by way of illustration and not limitation, hook and loop fasteners, adhesive fasteners, a compression system, locking keyways, screws, bolts, or other mechanical fasteners.

The surgical accessory bar, well known in the art, has a uniform cross-section and the adjustable securing device, in the open position, may be slid along the surgical accessory bar as desired. Therefore, in the preferred embodiment, the securing apparatus has the advantage of being anchorable at a plurality of points on the surgical accessory bar which surrounds a patient's head during intracranial surgery. The adjustable securing device is connected by a pivot assembly to a capture assembly that is configured to hold the elasticized band of a scalp hook retractor.

Thus, there is further disclosed a surgical retractor securing apparatus adapted to be releasably secured to a surgical accessory bar and operative to releasably retain an elasticized band, comprising: 1) an adjustable securing device for gripping the surgical accessory bar at a proximal end of the adjustable securing device formed with a device pivot assembly receiver; 2) an accessory bar compression adjuster secured to the adjustable securing device to grip and release the surgical accessory bar; 3) a capture assembly formed with a capture pivot assembly receiver to releasably retain the elasticized band; and 4) a pivot assembly for joining the capture assembly to the adjustable securing device.

In the preferred embodiment, the invention provides a capture assembly comprising a gripping cam that grips the elasticized band of a scalp hook retractor so that the band is compressed between the gripping cam and the surgical accessory bar. In application, the gripping cam is rotated about the pivot assembly away from the surgical accessory bar, the stretched elasticized band is placed in the gap between the gripping cam and the surgical accessory bar, and the cam is then rotated back into an engaged position compressing the elasticized band against the surgical accessory bar.

The cam gripping surface may be provided with a high friction surface to enhance the grip upon the elasticized band. In other embodiments, the cam may be formed with a smooth surface to which a disposable adhesive pad with a high grip surface may be affixed. The gripping cam provides a quick release method of fixation for the elasticized band that permits rapid fixation and precise tensioning by the surgeon, maintains the band in a fixed compressed position during surgery, and yet may be quickly and easily released at any time by rotating the cam away from the surgical accessory bar. In additional embodiments, the capture device may be formed, by way of illustration and not limitation, as a dual cam device or any of the widely known quick release mechanisms.

The gripping cam, in the preferred embodiment, is pivotably fastened to the adjustable securing device by means of a pivot assembly. The pivot assembly passes through the device pivot assembly receiver and the cam pivot assembly receiver. In one embodiment, the pivot assembly comprises a cam pivot pin that threads into a stud. The gripping cam is provided with a pin slot to receive the cam pivot pin and the adjustable securing device is provided with a stud engager to receive the stud. In the preferred embodiment, the cam pivot pin has an enlarged head at the distal end that prevents the cam pivot pin from passing through the pin slot of the gripping cam. The enlarged head may be adapted to engage a tool such as, by way of illustration and not limitation, a screwdriver or hex key.

The cam pivot pin may be threaded at the proximal end to engage the cooperating female threads in a stud recess. Alternative embodiments may include a cam pivot pin having a shoulder bolt thread that limits the depth to which the pin maybe threaded into the stud. This limitation ensures that the pivot assembly may be tightened only far enough to lightly hold the gripping cam against the adjustable securing device, and to prevent overtightening. The stud may be configured in a plurality of shapes such that the stud will not turn during tightening of the cam pivot pin. The stud may also be additionally configured with a stud base plate, to prevent the stud from being drawn through the adjustable securing device during the tightening process. In other embodiments, intended for illustration and not limitation, the pivot assembly may be formed by a fixed fastener, such as a rivet, by a shoulder bolt mated to a recess in the adjustable securing device containing cooperating female threads, or any other of the widely known mechanical fastening devices, such as a nut and bolt.

The present invention is also directed to a device for releasably retaining an elasticized band during surgery. Thus, there is disclosed a device for releasably retaining an elasticized band during surgery adapted to be releasably secured to a surgical accessory bar, comprising: 1) a means for adjustably gripping the surgical accessory bar; 2) a means for releasably capturing the elasticized band; and 3) a means for coupling the adjustable gripping means and the capturing means.

There is further disclosed a device for retracting tissue during surgery comprising of: 1) a means for releasable tissue engagement; 2) a means for imparting elastic tensile force on the tissue engagement means; and 3) a means for quick release anchoring of the tensile force means.

These variations, modifications, alternatives, and alterations of the various preferred embodiments, arrangements, and configurations may be used alone or in combination with one another as will become more readily apparent to those with skill in the art with reference to the following detailed description of the preferred embodiments and the accompanying figures and drawings.

BRIEF DESCRIPTION OF THE DRAWINGS

Without limiting the scope of the present invention as claimed below and referring now to the drawings and figures:

DESCRIPTION OF THE INVENTION

The surgical retractor securing apparatus of the instant invention provides a significant advance in the state of the art of anchoring surgical retractors. The preferred embodiments of the surgical retractor securing apparatus accomplish this by new and novel arrangements of elements that are configured in unique and novel ways and which demonstrate previously unavailable but preferred and desirable capabilities.

The detailed description set forth below in connection with the drawings is intended merely as a description of the presently preferred embodiments of the invention, and is not intended to represent the only form in which the present invention may be constructed or utilized. The description sets forth the designs, functions, means, and methods of implementing the invention in connection with the illustrated embodiments. It is to be understood, however, that the same or equivalent functions and features may be accomplished by different embodiments that are also intended to be encompassed within the spirit and scope of the invention.

Figure 1:
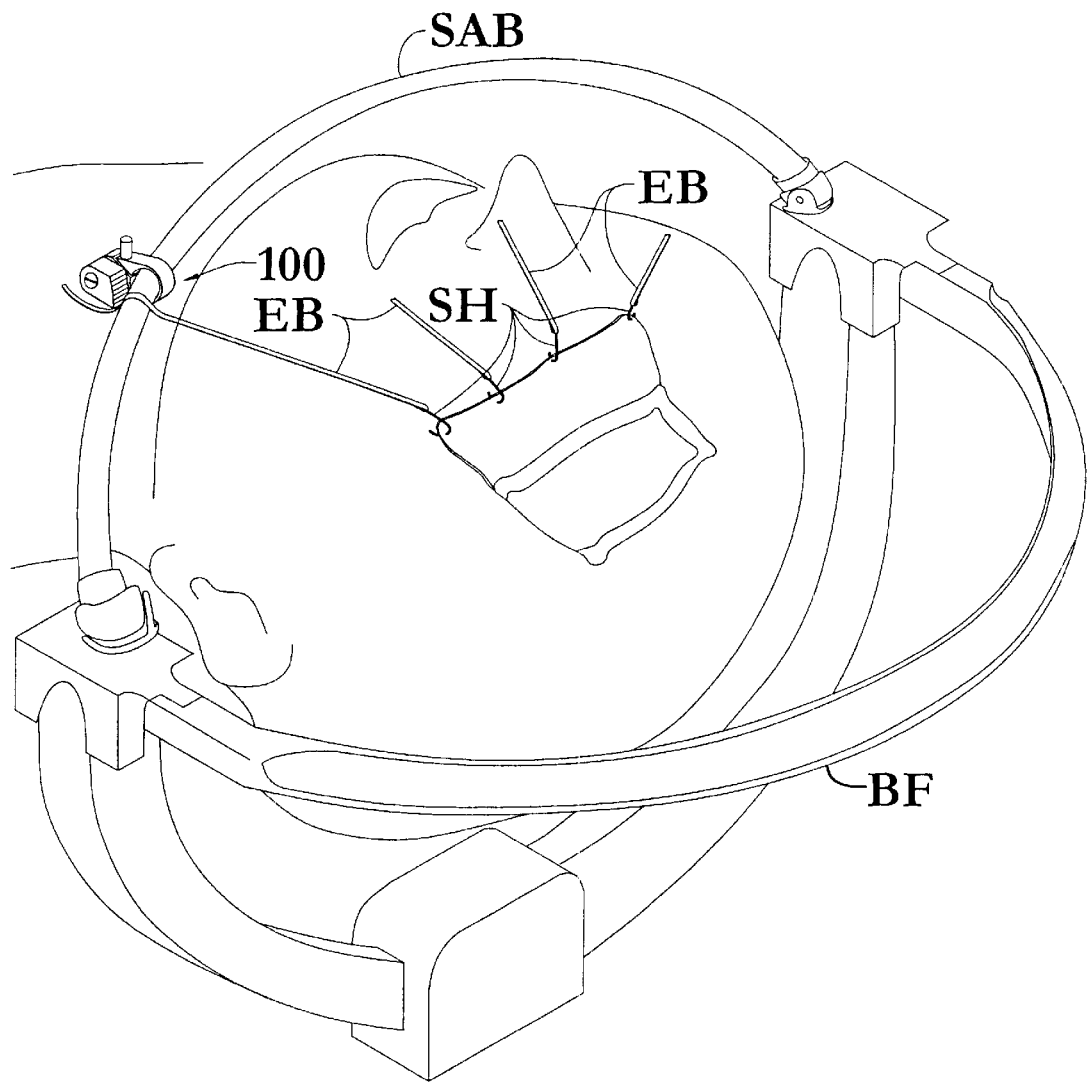
FIG. 1 is an elevated perspective view, in reduced scale, of a surgical retractor securing apparatus in place on the surgical accessory bar of a halo style head fixation device.
Figure 2:
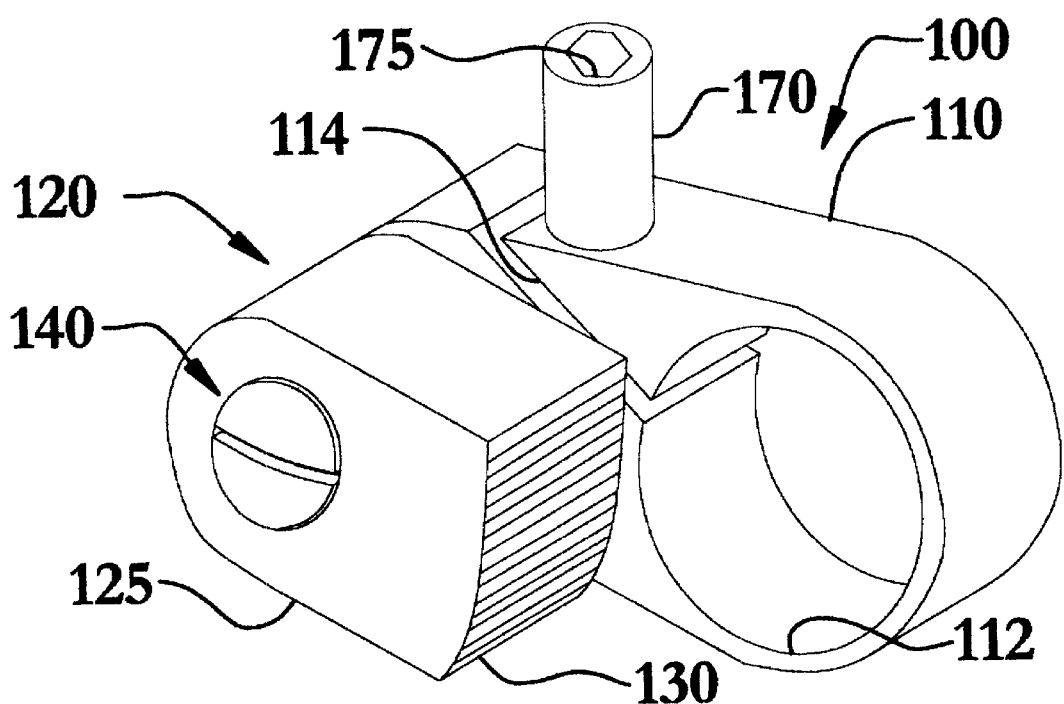
FIG. 2 is a detailed elevated perspective view, in enlarged scale, of the surgical retractor securing apparatus shown in FIG. 1.
Figure 3:
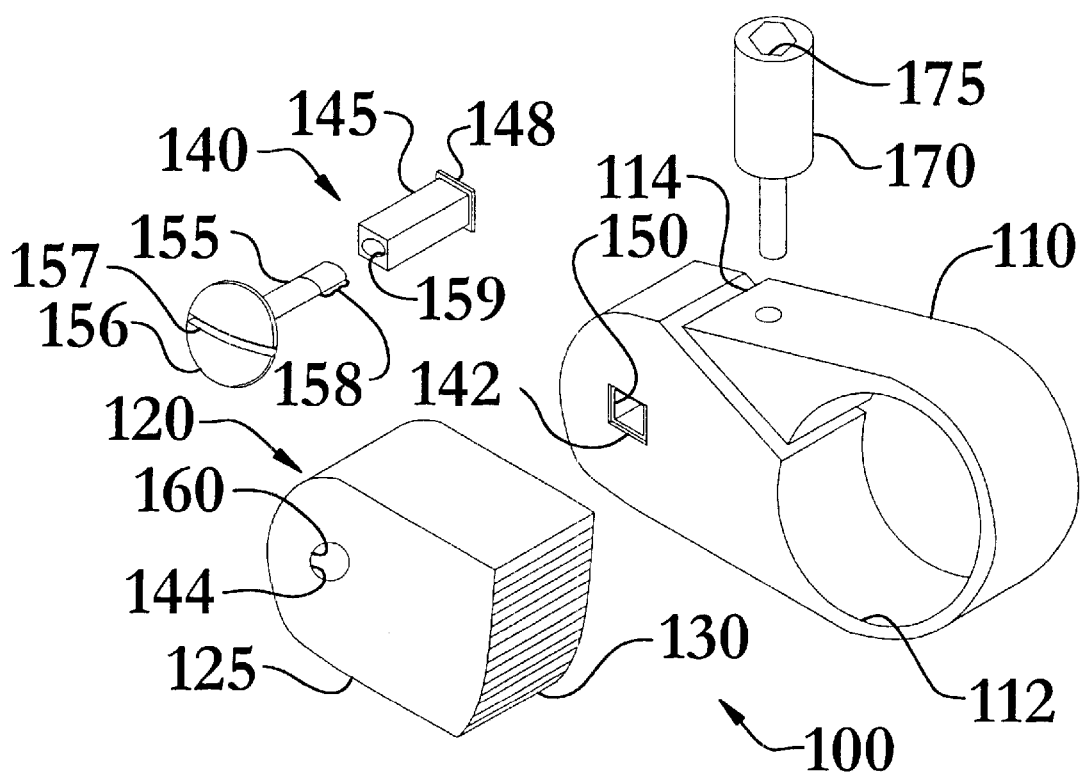
FIG. 3 is a detailed elevated perspective exploded view, in enlarged scale, of the surgical retractor securing apparatus shown in FIG. 1.

With reference generally now to FIGS. 1 through 5, and more specifically to FIGS. 2 and 3, in one of the many preferable arrangements, the surgical retractor securing apparatus 100 includes, among other elements, an adjustable securing device 110 and a capture assembly 120. As shown in FIG. 1, the surgical retractor securing apparatus 100 is designed to be secured to a surgical accessory bar SAB, or other external support, and releasably retain the elasticized band EB of a retractor while maintaining a continuous but adjustable tension on the skin or other tissue.

The adjustable securing device 110 is designed to grip and rigidly hold a surgical accessory bar SAB or other external support. The capture assembly 120 is designed to releasably retain the elasticized band EB of the scalp hook retractor.

In exemplary configurations, the adjustable securing apparatus 100 may be configured to define an adjustable accessory bar receiver 112 that substantially surrounds a surgical accessory bar SAB, as shown in FIG. 1, that is attached to the basal frame BF of a halo style head fixation device, well known in the art, used in intracranial neurosurgery. Referring again to FIGS. 1 and 2, the adjustable securing device 110 may include a securing device compression area 114 that can be manually compressed by a securing device compression adjuster 170. In one embodiment, the compression adjuster 170 may be threaded into the adjustable securing device 110 to provide a compressive grip on the surgical accessory bar SAB. The securing device compression adjuster 170, in the preferred embodiment, is provided with a thumbscrew and an adjuster tool engager 175 at its distal end such that a tool may be used to increase the leverage in tightening and loosening the securing device compression adjuster 170. In additional embodiments, the securing device compression adjuster 170 may include a thumbscrew configured with a high friction surface, wings, alternative shaped top with gripping edges, or other grip enhancing features.

Additionally, the adjustable securing device 110 may be configured to have a partially open position at rest, such that a manual release of the securing device compression adjuster 170 will result in a release of the compressive grip upon the surgical accessory bar SAB. In alternative embodiments, the adjustable securing device 110 may be configured to attach to any external support by an alternative mechanical gripping assembly, including, by way of illustration and not limitation, hook and loop fasteners, adhesive fasteners, a compression system, locking keyways, screws, bolts, or other mechanical fasteners.

With continued reference to the various figures and specifically now also to FIG. 1, the surgical accessory bar SAB, well known in the art, has a uniform cross-section and the adjustable securing device 110 in the open position may slide along the surgical accessory bar SAB to any desired location. Therefore, in the preferred embodiment, the surgical retractor securing apparatus 100 has the advantage of being anchorable at a plurality of points on the surgical accessory bar SAB which may surround a patient's head during intracranial surgery. Multiple units may be placed on a surgical accessory bar to utilize multiple skin hook SH retractors.

In the exemplary arrangement of the instant invention shown in FIGS. 2 and 3, the adjustable securing device 110 is connected by a pivot assembly 140 to a capture assembly 120 that is configured to hold the elasticized band EB of a scalp hook SH retractor. In the preferred embodiment, the invention provides a capture assembly 120 comprising a gripping cam 125 that grips the elasticized band EB of a scalp hook SH retractor so that the elasticized band EB is compressed between the gripping cam 125 and the surgical accessory bar SAB. The gripping cam 125 is capable of gripping elasticized bands EB of varying cross-sectional profiles, including, for example and not limitation, round, elliptical, square, or flat bands of varying thickness and widths.

Figure 4:
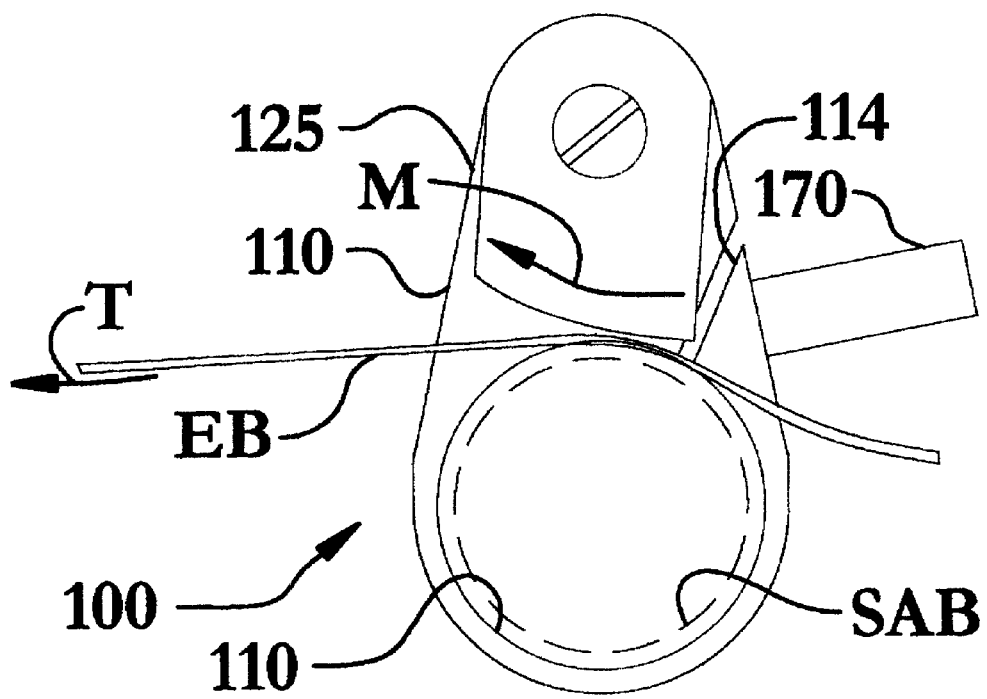
FIG. 4 is an elevation view, in enlarged scale, of the surgical retractor securing apparatus shown in FIG. 1., showing the capture assembly with the gripping cam in the engaged position.
Figure 5:
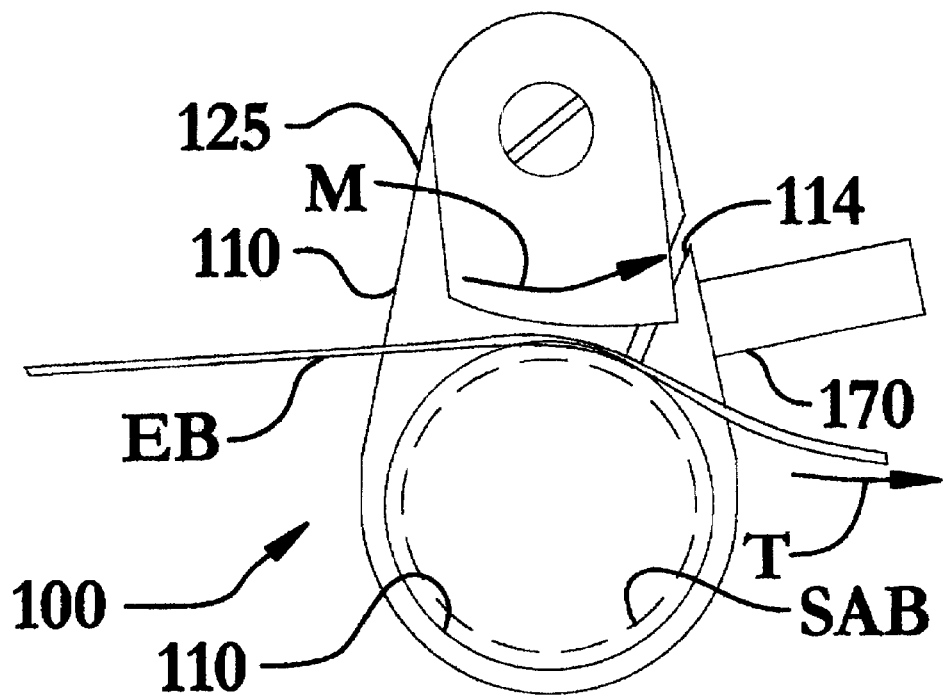
FIG. 5 is an elevation view, in enlarged scale, of the surgical retractor securing apparatus shown in FIG. 1., showing the capture assembly with the gripping cam in the unengaged position.

With reference now to FIG. 5; in application, the gripping cam 125 is rotated, as shown by directional arrow M, about the pivot assembly 140, away from the surgical accessory bar SAB to create a gap to receive the elasticized band EB between the gripping cam 125 and the surgical accessory bar SAB. The elasticized band EB is stretched, to produce tension along direction arrow T, and is placed in the gap between the gripping cam 125 and the surgical accessory bar SAB. Now referring to FIG. 4, the gripping cam 125 is rotated back into an engaged position compressing the elasticized band EB against the surgical accessory bar SAB. The gripping cam 125 thereby fixes the position of the elasticized band EB and maintains tension between the surgical retractor securing apparatus 100 and the scalp hook SH, as shown in FIG. 1. With reference now to FIG. 4, the tension exerted along direction arrow T assists in maintaining the engaged position of gripping cam 125. As tension increases along direction arrow T, the pressure exerted by the gripping cam 125 against the surgical accessory bar SAB is increased. Gripping cam 125 thus provides a firm grip across a wide plurality of tensions.

Referring now to FIGS. 2 and 3, the cam gripping surface 130 may be provided with a high friction surface to enhance the grip upon the elasticized band EB. The cam gripping surface 130 may, by way of example and not limitation, be formed with a striated surface, dimples, stipples, engraved pattern, or other friction enhancing surface finish. In other embodiments, the cam 125 may be formed with a smooth surface to which a disposable adhesive pad with a high grip surface may be affixed. The gripping cam 125 provides a quick release method of fixation for the elasticized band EB that permits rapid fixation and precise tensioning by the surgeon, maintains the band in a fixed compressed position during surgery, yet which may be quickly and easily released at any time by rotating the gripping cam 125 away from the surgical accessory bar SAB.

In additional embodiments, the capture assembly 120 may be formed, by way of illustration and not limitation, as a dual cam device or as any of the widely known quick release mechanisms, for gripping the elasticized band EB.

With reference to FIG. 3, the gripping cam 125, in the preferred embodiment, is pivotably fastened to the adjustable securing device 110 by means of a pivot assembly 140. The pivot assembly 140 passes through the device pivot assembly receiver 142 and the cam pivot assembly receiver 144. Such an embodiment allows the surgical retractor securing device 100 to be assembled with the gripping cam 125 secured to either side of the adjustable securing device 110.

Additional embodiments may include those where the pivot assembly 140 comprises a cam pivot pin 155 with a threaded stud engager 158 that threads into the cooperating female threads of the threaded receiver 159 of a stud 145. The gripping cam 125 is provided with a pin slot 160 to receive the cam pivot pin 155 and the adjustable securing device 110 is provided with a stud engager 150 to receive the stud 145. In the preferred embodiment, the cam pivot pin 155 has an enlarged head 156 at the distal end that prevents the cam pivot pin 155 from passing through the pin slot 160 of the gripping cam 125. The enlarged head 156 is formed with a tool engager 157 adapted to engage a tool, as for illustration and not limitation, such as a screwdriver or hex key.

The cam pivot pin 155 may be threaded at the proximal end to engage the cooperating female threads of the stud 145. Other embodiments include those where the cam pivot pin 155 may include a shoulder bolt thread that limits the depth to which the pin 155 maybe threaded into the cooperating female threads of the stud 145. The shoulder bolt ensures that the pivot assembly 140 may be tightened only far enough to lightly hold the gripping cam 125 against the adjustable securing device 110, and to prevent overtightening. The stud 145 may be configured in a plurality of shapes such that the stud 145 will not turn during tightening of the cam pivot pin 155. The stud 145 may additionally be configured with a stud base plate 148, to prevent the stud 145 from being drawn through the adjustable securing device 110 during the tightening process. Other embodiments, intended for illustration and not limitation, include the pivot assembly 140 being formed by a fixed fastener, such as a rivet, a shoulder bolt mated to cooperating female threads partially threaded into the adjustable securing device 110, or any other of the widely known mechanical fastening devices, such as a nut and bolt.

EXAMPLE

To demonstrate and evaluate the surgical retractor securing apparatus according to the invention, a procedure was conducted upon a cadaver. The cadaver head was fixated in a Spetzler Headrest in the usual fashion. A surgical accessory bar was attached and six securing apparatuses similar to FIG. 2, were placed on the bar and positioned parallel to the proposed entry site of the skull. A physician then made an incision on the skull and used the six scalp hooks with rubber bands to retract the scalp back from the wound site. The distal ends of the rubber bands were placed in the securing apparatuses under tension. The securing apparatuses all consistently held (locked) the rubber bands without slipping. The physician then proceeded to increase the load on the hooks by moving the accessory bar away from the incision site, thereby stretching the rubber bands. This was done to the point where physical damage to the scalp would normally occur. The rubber bands were held secure even under this "worst case" situation.

Numerous alterations, modifications, and variations of the preferred embodiments disclosed herein will be apparent to those skilled in the art and they are all anticipated and contemplated to be within the spirit and scope of the instant invention. For example, although specific embodiments have been described in detail, those with skill in the art will understand that the preceding embodiments and variations can be modified to incorporate various types of substitute and or additional or alternative materials, relative arrangement of elements, and dimensional configurations for compatibility with the myriad possible surgical retractor interventions and procedures. Accordingly, even though only few variations of the present invention are described herein, it is to be understood that the practice of such additional modifications and variations and the equivalents thereof, are within the spirit and scope of the invention as defined in the following claims.

The corresponding structures, materials, acts, and equivalents of all means or step plus function elements in the claims below are intended to include any structure, material, or acts for performing the functions in combination with other claimed elements as specifically claimed.

We claim:

1. A surgical retractor securing apparatus adapted to be releasably secured to a surgical accessory bar and operative to releasably retain an elasticized band, comprising:
    an adjustable securing device for gripping the surgical accessory bar at a proximal end of the adjustable securing device; and
    a capture assembly mounted at a distal end of the adjustable securing device for releasably retaining the elasticized band.

2. The apparatus according to claim 1, wherein an adjustable accessory bar receiver is formed in the adjustable securing device to releasably receive the surgical accessory bar.

3. The apparatus according to claim 1, wherein the adjustable securing device is further formed with a securing device compression area to allow the adjustable accessory bar receiver to contract and expand to grip and release the surgical accessory bar.

4. The apparatus according to claim 3, further comprising:
    an accessory bar compression adjuster to compress and release the securing device compression area.

5. The apparatus according to claim 1, wherein the capture assembly is formed with at least one gripping cam.

6. The apparatus according to claim 1, wherein the adjustable securing device is formed with a device pivot assembly receiver.

7. The apparatus according to claim 6, wherein the capture assembly is a gripping cam that releasably grips the elasticized band between the surgical accessory bar and the gripping cam which is formed with a cam pivot assembly receiver and secured to the adjustable securing device by a pivot assembly passing through the device pivot assembly receiver and the cam pivot assembly receiver.

8. The apparatus according to claim 7, wherein the gripping cam is formed to include a high friction gripping surface.

9. The apparatus according to claim 7, wherein the pivot assembly comprises a cam pivot pin wherein a proximal end is formed with an enlarged head and a tool engager and a distal end is formed with a threaded stud engager and a stud formed with a stud base plate at a distal end and a threaded receiver to releasably mate with the threaded stud engager at a proximal end.

10. The apparatus according to clam 7, wherein the pivot assembly comprises a shoulder bolt wherein a proximal end is formed with all enlarged head and a tool engager and a distal end is formed with a threaded device engager and the device pivot assembly receiver further includes a cooperating thread structure to receive the threaded device engager.

11. A surgical retractor securing apparatus adapted to be releasably secured to a surgical accessory bar and operative to releasably retain an elasticized band, comprising:
    an adjustable securing device for gripping the surgical accessory bar at a proximal end of the adjustable securing device formed with a device pivot assembly receiver;
    an accessory bar compression adjuster secured to the adjustable securing device to grip and release the surgical accessory bar;
    a capture assembly formed with a capture pivot assembly receiver to releasably retain the elasticized band; and
    a pivot assembly for joining the capture assembly to the adjustable securing device.

12. The apparatus according to claim 11, wherein an adjustable accessory bar receiver is formed in the adjustable securing device to releasably receive the surgical accessory bar.

13. The apparatus according to claim 11, wherein the adjustable securing device is further formed with a securing device compression area to allow the adjustable accessory bar receiver to contract and expand to grip and release the surgical accessory bar.

14. The apparatus according to claim 11, wherein the capture assembly is formed with at least one gripping cam.

15. The apparatus according to claim 11, wherein the capture assembly is a gripping cam that releasably grips the elasticized band between the surgical accessory bar and the gripping cam and is secured to the adjustable securing device by the pivot assembly passing through the device pivot assembly receiver and the capture pivot assembly receiver.

16. The apparatus according to claim 15, wherein the pivot assembly comprises a cam pivot pin formed with a pivot tool engager at a proximal end and a threaded stud engager at a distal end, and a stud formed with a stud base plate a distal end and a threaded receiver to releasably mate with the threaded stud engager at a proximal end.

17. A device for releasably retaining an elasticized band during surgery adapted to be releasably secured to a surgical accessory bar, comprising:
    a means for adjustably gripping the surgical accessory bar;
    a means for releasably capturing the elasticized band; and
    a means for coupling the adjustable gripping means and the capturing means.

18. The device for releasably retaining an elasticized band during surgery according to claim 17, wherein the adjustable gripping means further comprises a means for receiving a surgical accessory bar and a compression means to vary the pressure exerted by the adjustable gripping means on the surgical accessory bar.

19. The device for releasably retaining an elasticized band during surgery according to claim 17, wherein the capturing means includes an entrapment means for compressing the elasticized band between the entrapment means and the surgical accessory bar.

20. The device for releasably retaining an elasticized band during surgery according to claim 17, wherein the coupling means includes a pivoting means for rotatably joining the adjustable gripping means and the capturing means.

* * * * *